(12) United States Patent
Jaensch et al.

(10) Patent No.: US 7,906,686 B2
(45) Date of Patent: Mar. 15, 2011

(54) PROCESS FOR OXIDIZING ALKYLAROMATIC COMPOUNDS

(75) Inventors: Helge Jaensch, Houston, TX (US); Jihad M. Dakka, Whitehouse Station, NJ (US); Francisco M. Benitez, Houston, TX (US); Ulrich Kortz, Bremen (DE); Ryan Matthew Richards, Golden, CO (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/532,388

(22) PCT Filed: Apr. 7, 2008

(86) PCT No.: PCT/EP2008/002753
§ 371 (c)(1),
(2), (4) Date: Feb. 9, 2010

(87) PCT Pub. No.: WO2008/128638
PCT Pub. Date: Oct. 30, 2008

(65) Prior Publication Data
US 2010/0185016 A1 Jul. 22, 2010

Related U.S. Application Data

(60) Provisional application No. 60/925,221, filed on Apr. 19, 2007.

(51) Int. Cl.
C07C 45/53 (2006.01)
C07C 409/00 (2006.01)
C07C 37/00 (2006.01)
(52) U.S. Cl. ......... 568/385; 568/484; 568/575; 568/801
(58) Field of Classification Search .................. 568/385, 568/484, 575, 801
See application file for complete search history.

(56) References Cited

U.S. PATENT DOCUMENTS

| | | | |
|---|---|---|---|
| 2,573,947 | A | 11/1951 | Bell et al. |
| 2,630,456 | A | 3/1953 | Bell et al. |
| 5,183,945 | A | 2/1993 | Stibrany et al. |
| 5,334,780 | A | 8/1994 | Shaikh et al. |
| 5,922,920 | A | 7/1999 | Bond et al. |
| 6,720,462 | B2 | 4/2004 | Kuhnle et al. |
| 6,852,893 | B2 | 2/2005 | Kuhnle et al. |
| 2003/0083527 | A1 | 5/2003 | Kuhnle et al. |

FOREIGN PATENT DOCUMENTS

| | | |
|---|---|---|
| JP | 2002/282698 | 10/2002 |
| WO | 88/07745 | 10/1988 |
| WO | 03/028881 | 4/2003 |
| WO | 2006/015826 | 2/2006 |

OTHER PUBLICATIONS

Burns R. C. et al., "*Homogeneous-phase catalytic $H_2O_2$ Oxidation of Isobutyraldehyde Using Keggin, Dawson and Transition Metal-Substituted Lacunary Heteropolyanions*" Journal of Molecular Catalysis A : Chemical, 2002, vol. 184(1-2), pp. 451-464.

Cavani F. et al., "*Improvement of Catalytic performance in Isobutane Oxidation to Methacrylic Acid of Keggin-type Phosphomolybdates by Preparation via Lacunary Precursors: Nature of the Active Sites*" Catalysis Letters, 2001, vol. 75(1-2), pp. 99-105.

Cavani F. et al., "*Combined Effects of Sb-doping and of Preparation via Lacunary Precursor for P/Mo-based, Keggin-type Polyoxometalates, Catalysts for the Selective Oxidation of Isobutane to Methacrylic Acid*" Topics in Catalysis, 2003, vol. 23, No. 1-4, pp. 119-124.

Cheng J.C. et al., "*Process for Producing Phenol and Methyl Ethyl Keton*" U.S. Appl. No. 11/660,065, filed Aug. 5, 2005.

Finke R. G. et al., "*Autoxidation-Product-Initiated Dioxygenases: Vanadium-Based, Record Catalytic Lifetime Catechol Dioxygenase Catalysis*" Inorganic Chemistry 2005, vol. 44, pp. 8521-8530.

Haber J. et al., "*Catalytic Performance of the Dodecatungstophosphoric Acid on Different Supports*" Applied Catalysis A General, 2003, vol. 256, pp. 141-152.

Hill C. L. et al., "$[(Fe^{III}(OH_2)_2)_3(A\text{-}\alpha\text{-}PW_9O_{34})_2]^{9-}$ *on Cationic Silica Nanoparticles, a New Type of Material and Efficient Heterogeneous Catalyst for Aerobic Oxidations*" Journal of American Chemical Society, 2003, vol. 125(11), pp. 3194-3195.

Howard, J. A. et al., "*Absolute Rate Constants for Hydrocarbon Oxidation. VIII. The Reactions of Cumylperoxy Radicals*" Canadian Journal of Chemistry, 1968, vol. 46, pp. 1017-1022.

(Continued)

*Primary Examiner* — Sikarl A Witherspoon

(57) ABSTRACT

In a process for producing hydroperoxides, an alkylaromatic compound of general formula (I):

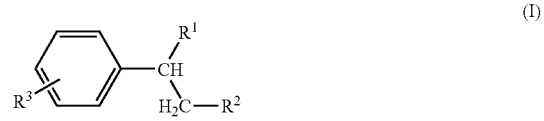

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, is contacted with oxygen in the presence of a catalyst comprising a polyoxometalate to produce a hydroperoxide of general formula (II):

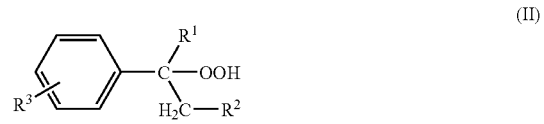

in which $R^1$, $R^2$ and $R^3$ have the same meaning as in formula (I) and wherein the polyoxometalate comprises a polyoxotungstate substituted with at least one further transition metal.

25 Claims, 4 Drawing Sheets

OTHER PUBLICATIONS

Howard, J. A. et al., "*Absolute Rate Constants for Hydrocarbon Oxidation. XI. The Reactions of Tertiary Peroxy Radicals*" Canadian Journal of Chemistry, 1968, vol. 46, pp. 2655-2660.

Howard, J. A. et al., "*Absolute Rate Constants for Hydrocarbon Autoxidation. XIV. Termination Rate Constants for Teritary Peroxy Radicals*" Canadian Journal of Chemistry, 1969, vol. 47, pp. 3793-3795.

Howard J. A. et al., "*Absolute Rate Constants for Hydrocarbon Autoxidation. XV. The induced decomposition of some t-hydroperoxides*" Canadian Journal of Chemistry 1969, vol. 47, pp. 3797-3801.

Kamat, K. et al., "*Efficient Epoxidation of Olefins with $\geq 99\%$ Selectivity and Use of Hydrogen Peroxide*" Science, 2003, vol. 300, pp. 964-966.

Krebs, B. et al., "*Syntheses and Crystal Structure Studies of Novel Selenium-and Tellurium-Substituted Lacunary Polyoxometalates*" Polyoxometallate Chemistry 2001, pp. 89-99.

Li, Ming-Qiang et al., "*Lacunary Keggin Polyoxotungstate as Reaction-Controlled Phase-transfer Catalyst for Catalytic Epoxidation of Olefins*" Chinese Journal of Chemistry, 2004, vol. 22(8), pp. 874-876.

Neumann, R. et al., "*Molecular Oxygen Activation by a Ruthenium-Substituted "Sandwich" Type Polyoxometalate*" Journal of American Chemical Society, 1998 vol. 120, pp. 11969-11976.

Neumann R. et al., "*A Highly Chemoselective, Diastereoselective, and Regioselective Epoxidation of Chiral Allylic Alcohols with Hydrogen Peroxide, Catalyzed by Sandwich-Type Polyoxometalates: Enhancement of Reactivity and Control of Selectivity by the Hydroxy Group through Metal-Alcoholate Bonding*" Journal of Organic Chemistry, 2003, vol. 68(5), pp. 1721-1728.

Neumann, R. et al. "*Noble Metal ($Ru^{III}$, $Pd^{III}$, $Pt^{II}$) Substituted "Sandwhich" Type Polyoxometalates: Preparation, Characterization, and Catalytic Activity in Oxidations of Alkanes and Alkenes by Peroxides*" Inorganic Chemistry, 1995, vol. 34, pp. 5753-5760.

Pope M.T. et al., "*Lacunary Polyoxometalate Anions Are $\pi$-Acceptor Ligands. Characterization of Some Tungsioruthenate (II, III, IV, V) Heteropolyanions and Their Atom-Transfer Reactivity*" Journal of American Chermical Society, 1992, vol. 114, pp. 2932-2938.

Ratiu C. et al., "*Synthesis and Characterization of $K_6[Ti(H_2O)P_2MoW_{16}O_{61}]$ $17H_2O$, a Ti (IV) Derivative of Monolacunary Well-Dawson 16-tungsto-molybdo-2-phosphate*" Polyhedron, 2002, vol. 21(4), 353-358.

Server-Carrio J. et al., "*Synthesis Characterization and Catalysis of $\beta_3$-$[Co^{II}O_4]$ $W_{11}O_{31}(O_2)_4]$, $^{10-}$ the First Keggin-Based True Heteropoly Dioxygen (Peroxo) Anion. Spectroscopic (ESR, IR) Evidence for the Formation of Superoxo Polytungstates*" Journal of American Chemical Society, 1999, vol. 121(5), pp. 977-984.

Sheldon, Roger A. et al, "*Organocatalytic Oxidations Mediated by Nitroxyl Radicals*" Adv. Synth. Catal., 2004, vol. 346, pp. 1051-1071.

Sousa F. L. et al., "*Novel Cerium (IV) Heteropolyoxotungstate Containing Two Types of Lacunary Keggin Anions*" Chemical Communication, 2004, vol. 23, pp. 2656-2657.

Villanneau R. et al., "*Co-ordination Chemistry of Lacunary Lindqvist-type Polyoxometalates:Cubic vs. Square-antiprismatic co-ordination*" Journal of Chem. Soc., 1999, vol. 3, pp. 421-426.

Yen, Yen-Chen, "*Phenol*" Process Economics Report No. 22B published by tyhe Stanford Research Institute in Dec. 1977, pp. 113-121 and 261-263.

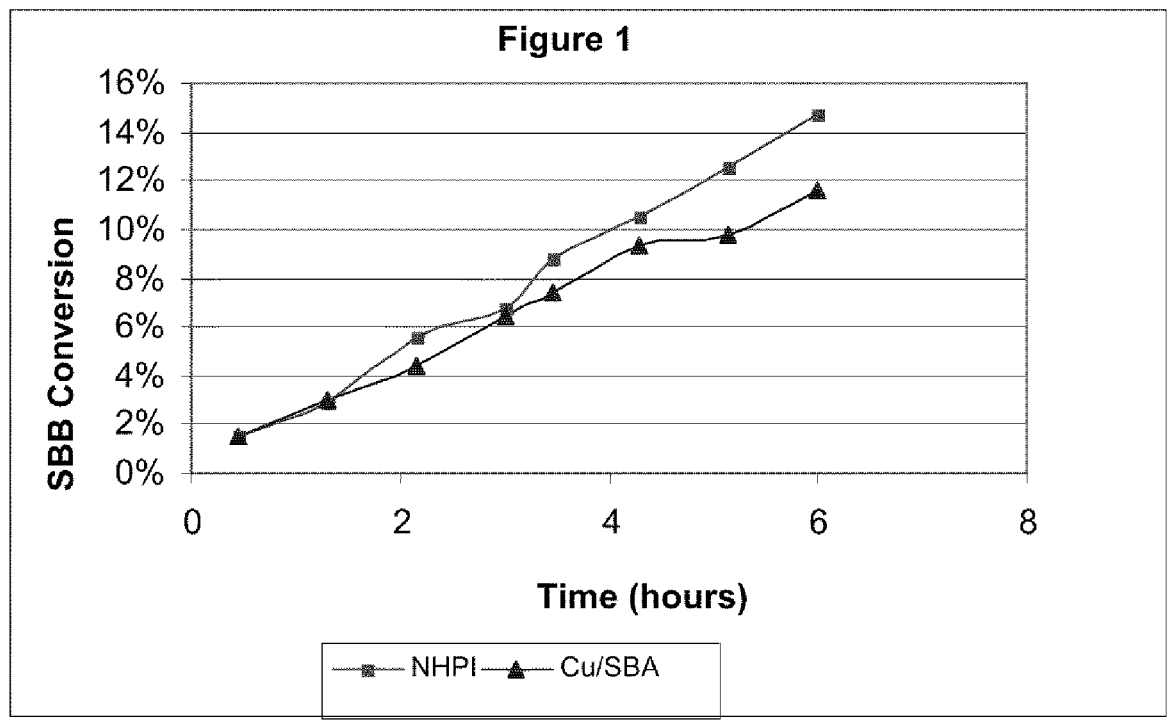
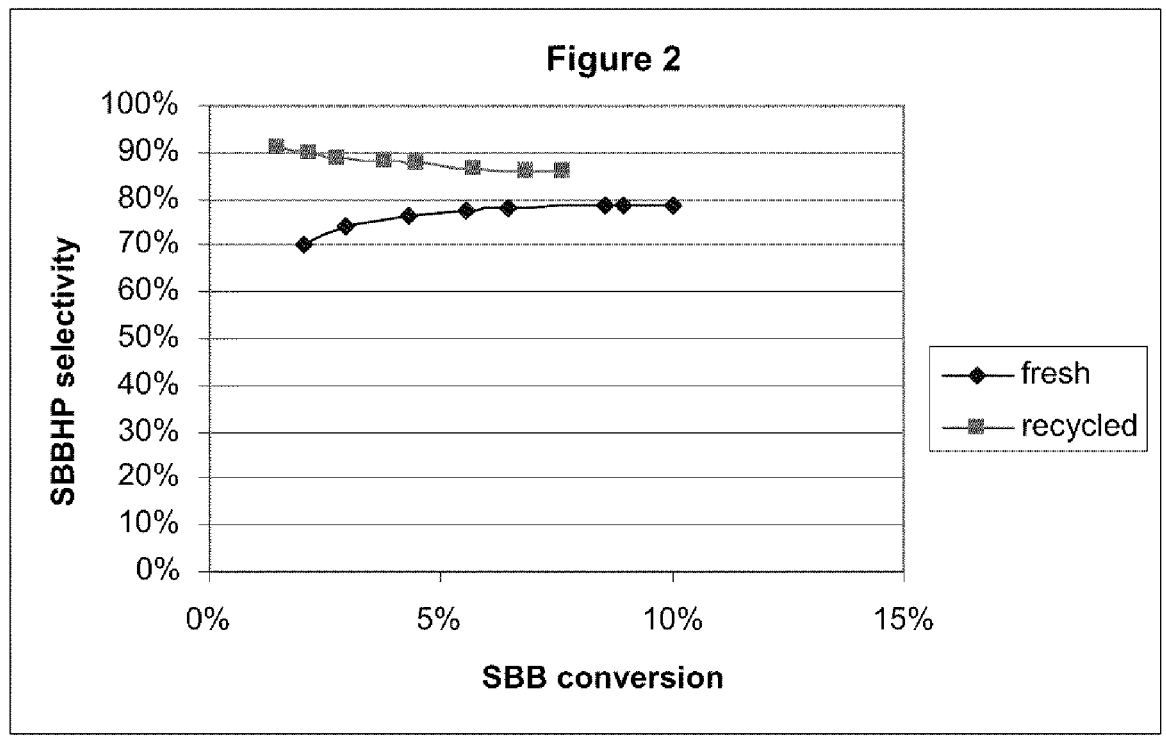

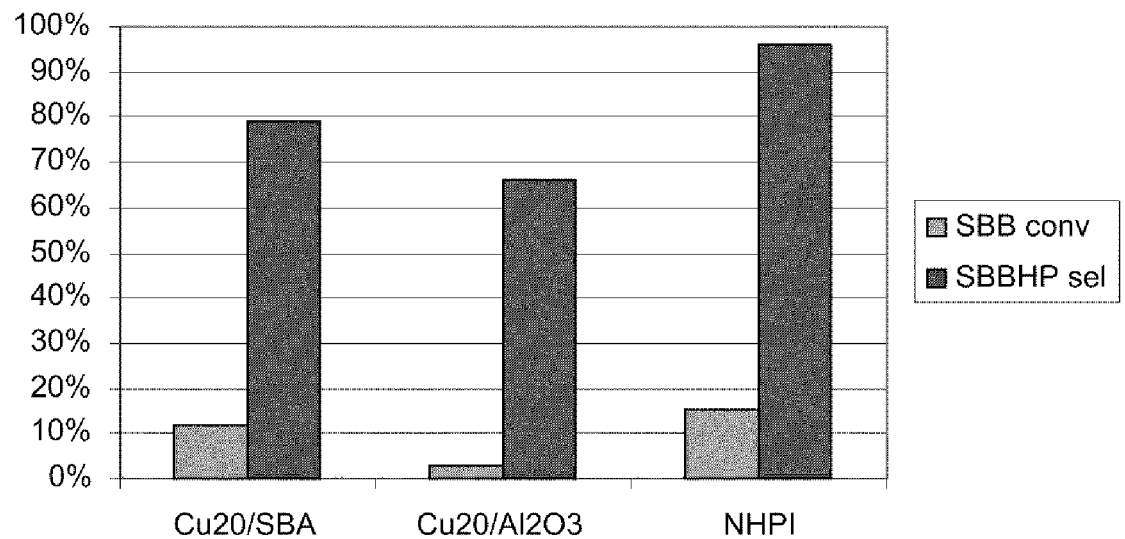
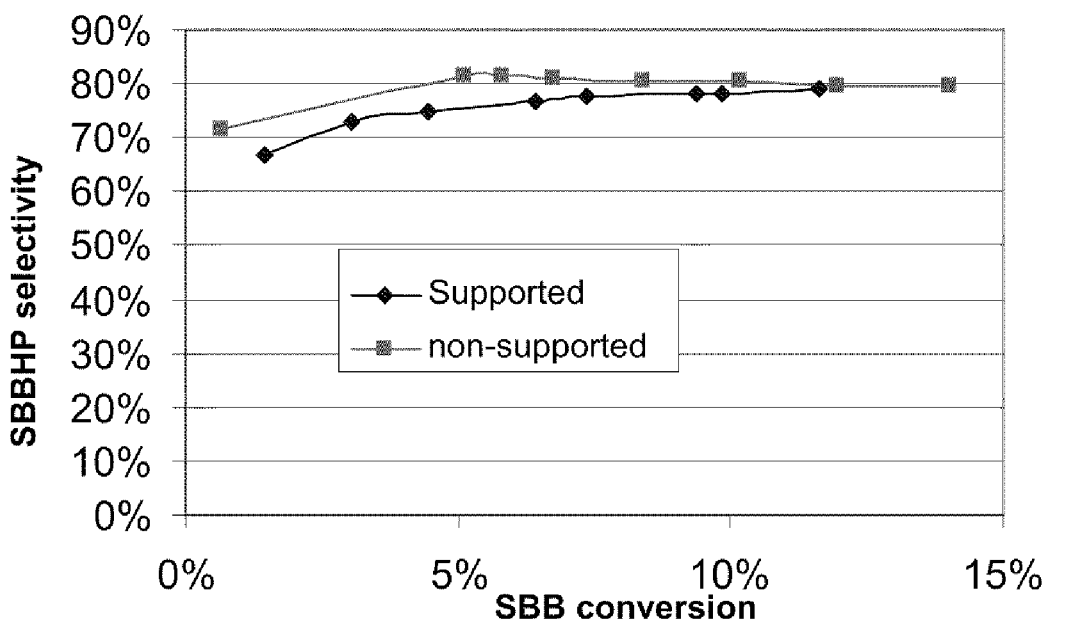

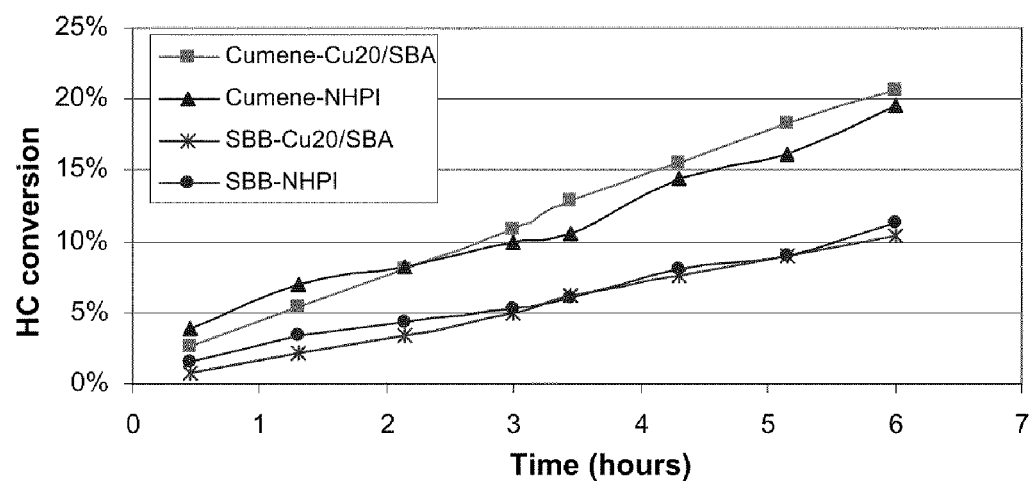
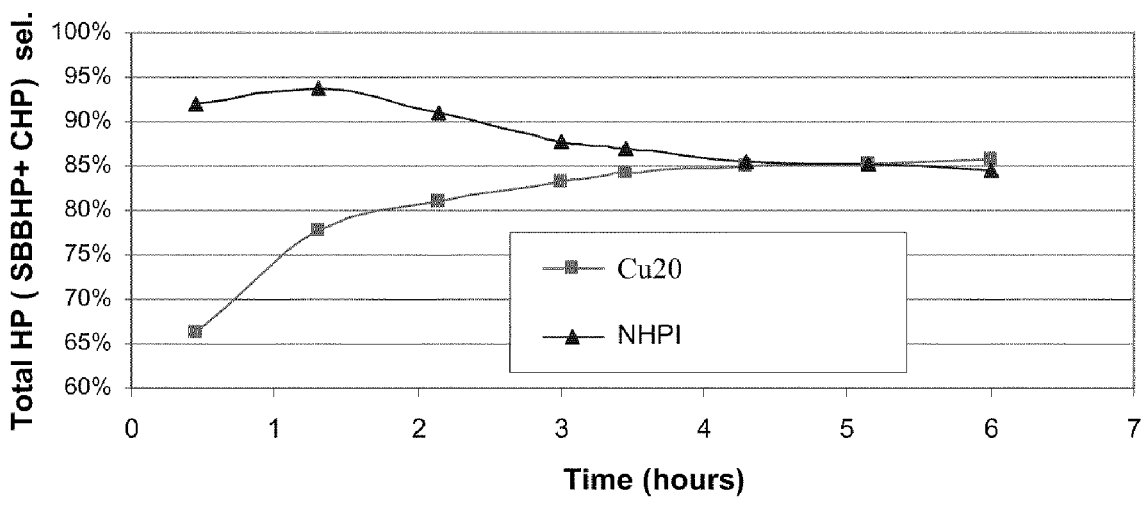

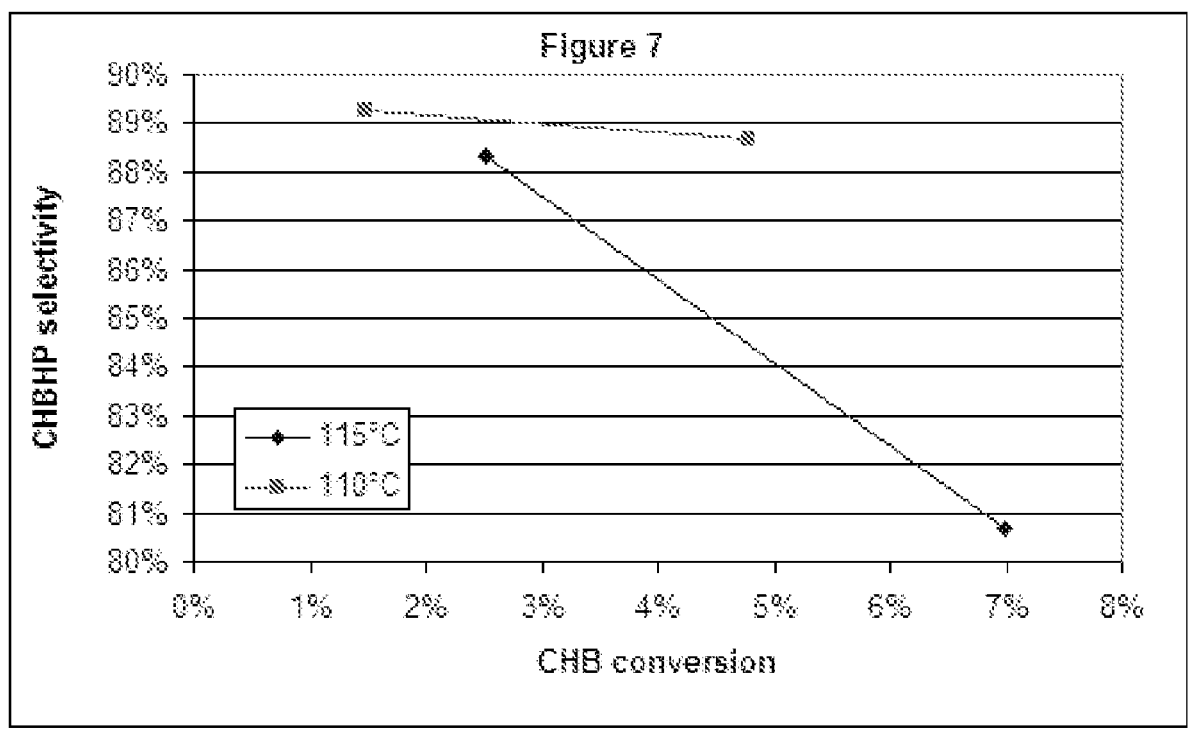

PROCESS FOR OXIDIZING ALKYLAROMATIC COMPOUNDS

PRIORITY CLAIM

This application claims the benefit of prior U.S. provisional application Ser. No. 60/925,221 filed Apr. 19, 2007, and International Patent Cooperation Treaty Application No. PCT/EP2008/002753 filed Apr. 7, 2008, both of which are hereby incorporated by reference in their entirety.

FIELD

The present invention relates to a process for oxidizing alkylaromatic compounds, and in one embodiment includes a process for producing phenols from the oxidation product.

BACKGROUND

Phenol and substituted phenols are important products in the chemical industry and are useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that of butenes is likely to increase, due to a developing shortage of propylene.

Thus, a process that uses butenes or higher alkenes instead of propylene as feed and that coproduces methyl ethyl ketone (MEK) or higher ketones, such as cyclohexanone, rather than acetone may be an attractive alternative route to the production of phenols. For example, there is a growing market for MEK, which is useful as a lacquer, a solvent and for dewaxing of lubricating oils. In addition, cyclohexanone is used as an industrial solvent, as an activator in oxidation reactions and in the production of adipic acid, cyclohexanone resins, cyclohexanone oxime, caprolactam and nylon 6.

It is known that phenol and MEK can be produced from sec-butylbenzene, in a process where sec-butylbenzene is oxidized to obtain sec-butylbenzene hydroperoxide and the peroxide decomposed to the desired phenol and methyl ethyl ketone. An overview of such a process is described on pages 113-121 and 261-263 of Process Economics Report No. 22B entitled "Phenol", published by the Stanford Research Institute in December 1977.

However, in comparison to cumene, oxidation of aromatic compounds substituted by branched alkyl groups having 4 or more carbon atoms, such as sec-butylbenzene, to the corresponding hydroperoxide requires higher temperatures and is very sensitive to the presence of impurities. For example, in the case of sec-butylbenzene containing 1% by weight of isobutylbenzene, the rate of formation of sec-butylbenzene hydroperoxide decreases to about 91% of that when the sec-butylbenzene is free of isobutylbenzene. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as low as about 82%.

Thus there is a need to find an oxidation process for producing for example $C_4+$ alkyl aromatic hydroperoxides, and particularly sec-butylbenzene hydroperoxide, that is much less sensitive to the presence of impurities than the existing oxidation processes, and that allows efficient commercial scale production of phenol and MEK or higher ketones.

U.S. Pat. Nos. 6,852,893 (Creavis) and 6,720,462 (Creavis) describe methods for producing phenol by catalytic oxidation of alkylaromatic hydrocarbons to the corresponding hydroperoxide, and subsequent cleavage of the hydroperoxide to give phenol and a ketone. Catalytic oxidation takes place with oxygen, in the presence of a free radical initiator and a catalyst, typically an N-hydroxycarbodiimide catalyst, such as N-hydroxyphthalimide. Preferred substrates that may be oxidized by this process include cumene, cyclohexylbenzene, cyclododecylbenzene and sec-butylbenzene.

In addition, the article by Sheldon et al entitled "Organocatalytic Oxidations Mediated by Nitroxyl Radicals" in *Adv. Synth. Catal.*, 2004, 346, pages 1051-1071 discloses that cyclohexylbenzene (CHB) can be oxidized to the 1-hydroperoxide with 97.6% selectivity at 32% CHB conversion at 100° C. in the presence of 0.5 mol % of a N-hydroxyphthalimide catalyst and 2 mol % of the product hydroperoxide as a free radical initiator.

However, while N-hydroxycarbodiimides have shown activity and selectivity for the oxidation of alkylaromatic compounds to their corresponding hydroperoxides, they suffer from the problems inherent in any homogeneous catalyst in that they tend to be removed from the reaction zone with the product effluent and so must be separated from the product effluent. There is therefore significant interest in developing a heterogeneous oxidation catalyst for producing alkylaromatic hydroperoxides provided adequate activity and selectivity can still be maintained.

In our International Patent Publication No. WO 06/15826 we have described a process for producing phenol and methyl ethyl ketone, in which a feed comprising benzene and a $C_4$ alkylating agent is contacted under alkylation conditions with catalyst comprising zeolite beta or a molecular sieve having an X-ray diffraction pattern including d-spacing maxima at 12.4±0.25, 6.9±0.15, 3.57±0.07 and 3.42±0.07 Ångstrom to produce an alkylation effluent comprising sec-butylbenzene. The sec-butylbenzene is then oxidized to produce a hydroperoxide and the hydroperoxide is cleaved to produce the desired phenol and methyl ethyl ketone. Although homogeneous catalysts, such as N-hydroxy substituted cyclic imides, are disclosed as suitable for the oxidation reaction, preferred catalysts are said to be heterogeneous catalysts, such as the oxo (hydroxo) bridged tetranuclear manganese complexes described in U.S. Pat. No. 5,183,945 and U.S. Pat. No. 5,922,920.

Another class of compounds that have been widely described as catalysts, including oxidation catalysts, are polyoxometalates ("POM's"), which are described in Pope et al., Heteropoly and Isopoly Oxometalates: Inorganic Chemistry Concepts, Springer-Verlag, New York (1983), incorporated herein by reference. Pope et al. and others have described numerous uses of POM's in catalysis such as oxidation of propylene and isobutylene to acrylic and methacrylic acids, oxidation of aromatic hydrocarbons; olefin polymerization; ammoxidation; oxidation of crotonaldehyde or butadiene to furan; dehydration of alcohols; oxidative coupling of alkyl benzenes or heterocycles; epoxidation; and hydrodesulfurization.

According to the invention, it has now been found that certain tungsten-containing polyoxometalates show activity and selectivity as catalysts in the oxidation of secondary alkyl substituted benzenes, including sec-butylbenzene and cyclohexylbenzene, to the corresponding hydroperoxides.

SUMMARY

In one aspect, the present invention resides in a process for oxidizing an alkylaromatic compound to the corresponding hydroperoxide, the process comprising contacting an alkylaromatic compound of general formula (I):

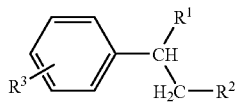

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a polyoxometalate, wherein the polyoxometalate comprises a polyoxotungstate substituted with at least one further transition metal.

In one embodiment the process of the invention further comprises converting the hydroperoxide into a phenol and an aldehyde or ketone of the general formula $R^1COCH_2R^2$ (III) in which $R^1$ and $R^2$ have the same meaning as in formula (I). Accordingly, in a further preferred aspect, the present invention resides in a process for producing a phenol, said process comprising:

(a) contacting an alkylaromatic compound of general formula (I):

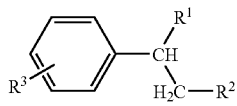

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a polyoxometalate to produce a hydroperoxide of general formula (II):

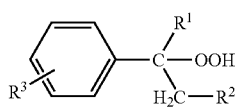

(II)

in which $R^1$, $R^2$ and $R^3$ have the same meaning as in formula (I) and wherein the polyoxometalate comprises a polyoxotungstate substituted with at least one further transition metal, and (b) converting the hydroperoxide of formula (II) into a phenol and an aldehyde or ketone of the general formula $R^1COCH_2R^2$ (III), in which $R^1$ and $R^2$ have the same meaning as in formula (I).

Conveniently, said alkylaromatic compound of general formula (I) is selected from ethylbenzene, cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene, with sec-butylbenzene and cyclohexylbenzene being preferred.

Conveniently, said at least one further transition metal is selected from copper, manganese, iron, cobalt, nickel, zinc, cadmium, ruthenium and mercury.

Conveniently, said polyoxotungstate also contains at least one element from Groups 13 to 15 of the Periodic Table of Elements, such as antimony, arsenic, bismuth, silicon, boron and phosphorus.

Conveniently, said contacting is conducted at a temperature of about 50° C. to about 200° C., such as about 90° C. to about 125° C. The contacting is conveniently conducted at a pressure of about 15 kPa to about 1000 kPa, preferably about 15 kPa to about 500 kPa, more preferably about 40 kPa to about 250 kPa and most preferably about 100 kPa to about 200 kPa.

Conveniently, the optional converting of the hydroperoxide to phenol and an aldehyde or ketone [hydroperoxide converting step (b) in the preferred aspect detailed above] is conducted in the presence of a catalyst, such as a homogeneous catalyst, for example at least one of sulfuric acid, perchloric acid, phosphoric acid, hydrochloric acid, p-toluenesulfonic acid, ferric chloride, boron trifluoride, sulfur dioxide and sulfur trioxide.

Alternatively, the hydroperoxide converting may be conducted in the presence of a heterogeneous catalyst, such as a smectite clay.

Conveniently, the hydroperoxide converting [step (b) in the above aspect] is conducted at a temperature of about 40° C. to about 120° C. and/or a pressure of about 100 to about 1000 kPa and/or a liquid hourly space velocity (LHSV) based on the hydroperoxide of about 1 to about 50 $hr^{-1}$.

BRIEF DESCRIPTION OF THE DRAWINGS

FIG. 1 is a graph comparing sec-butylbenzene (SBB) conversion (%) against time on stream (hours) for the N-hydroxyphthalimide (NHPI) catalyst used in Example 29 and for the $K_{12}Li_{13}[Cu_{20}Cl(OH)_{24}(H_2O)_{12}(P_8W_{48}O_{184})].22H_2O$ (abbreviated as $Cu_{20}P_8W_{48}$)/SBA-15 catalyst of Example 30.

FIG. 2 is a graph of sec-butylbenzene conversion against sec-butylbenzene hydroperoxide (SBBHP) selectivity (wt %) for the fresh $Cu_{20}P_8W_{48}$/SBA-15 catalyst of Example 30 and the recycled $Cu_{20}P_8W_{48}$/SBA-15 catalyst of Example 31.

FIG. 3 is a graph comparing sec-butylbenzene conversion and sec-butylbenzene hydroperoxide selectivity (sel) for the N-hydroxyphthalimide (NHPI) catalyst used in Example 29, the $Cu_{20}P_8W_{48}$/SBA-15 (abbreviated in the Figure as Cu20/SBA) catalyst of Example 30 and the $Cu_{20}P_8W_{48}$/$Al_2O_3$ (abbreviated in the Figure as Cu 20/Al2O3) catalyst of Example 32.

FIG. 4 is a graph of sec-butylbenzene conversion against sec-butylbenzene hydroperoxide selectivity for the $Cu_{20}P_8W_{48}$/SBA-15 catalyst of Example 30 and the unsupported $Cu_{20}P_8W_{48}$ catalyst of Example 33.

FIG. 5 is a graph of hydrocarbon (HC) conversion against time on stream (hours) for the oxidation of a sec-butylbenzene/cumene mixture using the N-hydroxyphthalimide (NHPI) catalyst used in Example 34 and the unsupported $Cu_{20}P_8W_{48}$ catalyst of Example 35.

FIG. 6 is a graph of total hydroperoxide (SBBHP and CHP) selectivity (sel), where CHP stands for cumene hydroperoxide, against time on stream for the oxidation of a sec-butylbenzene/cumene mixture using the N-hydroxyphthalimide (NHPI) catalyst used in Example 34 and the unsupported $Cu_{20}P_8W_{48}$ catalyst of Example 35 [abbreviated in the Figure as Cu20].

FIG. 7 is a graph of cyclohexylbenzene (CHB) conversion against cyclohexylbenzene hydroperoxide (CHBHP) selectivity (wt %) for the $Cu_{20}P_8W_{48}$ catalyst used at two temperatures in Example 36.

DETAILED DESCRIPTION OF THE EMBODIMENTS

As used herein, the Periodic Table of Elements is the version as set out in Chemical and Engineering News, 63(5), 27 (1985).

The present invention provides a process for oxidizing an alkylaromatic compound of general formula (I):

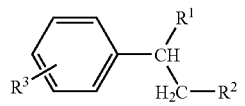

(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group. The phrase "provided that $R^1$ and $R^2$ may be joined" and so on is used herein to mean that, as an alternative to each of $R^1$ and $R^2$ being a ("monovalent") alkyl group, the two "alkyl" entities designated "$R^1$" and "$R^2$" are joined into a ("divalent") hydrocarbyl chain (having 2 to 8 carbons in that chain), with respective ends of that "divalent" chain begin linked to the C atoms specifically shown in formula (I) to form a ring. Thus, in an embodiment, $R^1$ and $R^2$ together constitute a hydrocarbyl moiety that connects to the carbon atoms of formula (I) form a cyclic group having from 4 to 10 carbon atoms, conveniently a cyclohexyl group, which may be substituted with one or more alkyl group having from 1 to 4 carbon atoms or with one or more phenyl groups. Examples of suitable alkylaromatic compounds are ethylbenzene, cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (I) is sec-butylbenzene and is produced by alkylating benzene with at least one $C_4$ alkylating agent under alkylation conditions and in the presence of a heterogeneous catalyst, such as zeolite beta or more preferably at least one molecular sieve of the MCM-22 family (as defined below). The alkylation conditions conveniently include a temperature of from about 60° C. to about 260° C., for example between about 100° C. and about 200° C. and/or a pressure of 7000 kPa or less, for example from about 1000 to about 3500 kPa and/or a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (I) is cyclohexylbenzene and is preferably produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. and/or a pressure of about 100 to about 7000 kPa and/or a benzene to hydrogen molar ratio of about 0.01 to about 100 and/or a WHSV of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, whose unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Ångstrom. The X-ray diffraction data used to characterize the material are obtained by standard techniques using the K-alpha doublet of copper as incident radiation and a diffractometer equipped with a scintillation counter and an associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared to the other butylbenzene isomers. Preferably, the molecular sieve is selected from (a) MCM-49, (b) MCM-56 and (c) isotypes of MCM-49 and MCM-56, such as ITQ-2.

The oxidation step of the present process is effected by contacting the alkylaromatic compound of general formula (I) with oxygen, for example in the form of a gas containing molecular oxygen, such as air, in the presence of a catalyst comprising a polyoxometalate ("POM"), wherein the POM is a polyoxotungstate substituted with at least one further transition metal. As used herein, the term "polyoxometalate" or "POM" is intended to mean a compound comprising polyoxoanion of at least one primary framework atom, in the present case tungsten, wherein the tungsten is partially substituted by at least one further transition metal. Suitable further transition metals include copper, manganese, iron, cobalt, nickel, zinc, cadmium, ruthenium and mercury. In general, POMs can be subdivided into heteropolyanions, which contain hetero atoms in addition to the primary framework atoms, and isopolyanions, which do not contain hetero atoms. Suitable hetero atoms include at least one element from Groups 13 to 15 of the Periodic Table of Elements, such as antimony, arsenic, bismuth, silicon, boron and phosphorus. Most of the POMs known are isolated as salts, with the most common counter cations being alkali metal ions and ammonium or mixtures thereof. In the rare case that all counterions are exclusively protons, then the material is referred to as a free polyoxometalate.

POMs are known to exist in a variety of structures including the Keggin, Wells-Dawson and Anderson-Evans structures. The different structures correspond to the specific geometry of particular POM compositions and vary according to the chemical nature and the coordination chemistry of the addenda and hetero atoms present, as well as their concentrations, ratios, pH etc. A major subclass of POMs useful in the present process is constituted by Keggin-type POMs. These polyoxoanions generally consists of 12 framework metals M and 40 oxygen atoms symmetrically arranged around a central hetero atom X and thus can be represented by the formula $X^nM_{12}O_{40}^{(8-n)-}$. If the hetero atom X has a lone pair of electrons (e.g. $As^{III}$, $Sb^{III}$), then the formation of such closed Keggin units is not allowed. In fact, most of these POMs consist of dimeric adducts of incomplete (lacunary) Keggin fragments joined together by extra framework or hetero atoms.

For example, Krebs et al. (Chem. Eur. J. 1997, 3, 1232; Inorg. Chem. 1999, 38, 2688) describe the dimeric structural type $[(WO_2)_4(OH)_2(\beta-XW_9O_{33})_2]^{12-}$ ($X=Sb^{III}$, $Bi^{III}$). Moreover, the authors were also able to substitute the two external tungsten atoms by first-row transition metals resulting in transition metal substituted polyoxometalates (TM-SPs) represented by the formula $[(WO_2)_2M_2(H_2O)_6(\beta-XW_9O_{33})_2]^{(14-2n)-}$ ($X=Sb^{III}$, $M^{n+}=Mn^{2+}$, $Fe^{3+}$, $Co^{2+}$, $Ni^{2+}$; $X=Bi^{III}$, $M^{n+}=Fe^{3+}$, $Co^{2+}$, $Ni^{2+}$, $Cu^{2+}$, $Zn^{2+}$).

Moreover, Kortz et al. report on tetrasubstituted dimeric polyoxotungstates which consist of two $[\beta-XW_9O_{33}]^{n-}$ (n=9, $X=As^{III}$, $Sb^{III}$; n=8, $X=Se^{IV}$, $Te^{IV}$) moieties linked by four $Fe^{3+}$ ions having terminal $H_2O$ ligands (Inorg. Chem. 2002, 41, 783). These authors were also able to substitute the iron centers in this structure by a large number of other $1^{st}$, $2^{nd}$ and $3^{rd}$ row transition metals (e.g. $Mn^{2+}$, $Co^{2+}$, $Ni^{2+}$, $Cd^{2+}$, $Hg^{2+}$).

Another POM structure useful in the present process is the so-called "copper-20 wheel structure". Thus interaction of $CuCl_2$ with $K_{28}Li_5$-$[H_7P_8W_{48}O_{184}]$ in the ratio 24:1 in aqueous medium (pH 6) results in the large, wheel-shaped $[Cu_{20}Cl(OH)_{24}(H_2O)_{12}(P_8W_{48}O_{184})]^{25-}$ (1), Mal, S. S.; Kortz, U. Angew. Chem. Int. Ed. 2005, 44, 3777-3780. Polyanion 1 crystallizes as a mixed potassium-lithium salt in the tetragonal system (space group I4/m). Polyanion 1 is unprecedented in structure, size and composition. This molecule represents the first transition metal substituted derivative of $[H_7P_8W_{48}O_{184}]^{33-}$ and it incorporates more $Cu^{2+}$ ions than any other POM known to date. The structure of the wheel-shaped $[H_7P_8W_{48}O_{184}]^{33-}$ precursor is maintained in 1 and the cavity has been filled with a highly symmetrical copper-hydroxo cluster. This emphasizes that the template effect plays an important role during formation of 1. We have shown that the oxo-groups in the cavity of the tungstophosphate precursor $[H_7P_8W_{48}O_{184}]^{33-}$ actually do interact with transition metal ions in aqueous medium, but some heating is required. Therefore, $[H_7P_8W_{48}O_{184}]^{33-}$ can indeed be considered as a superlacunary polyanion precursor and we expect that other transition metal ions besides copper(II) can also be incorporated.

The Cu20 cluster in 1 is composed of only 3 structurally unique types of copper(II) ions (8 octahedral, 4 square-pyramidal, 8 square-planar). All 20 copper centers are bridged to neighboring copper ions via $\mu_3$-oxo ligands resulting in a highly symmetrical, cage-like assembly. Based on bond valence sum calculations all 24 bridging oxygens are mono-protonated. Interestingly, the center of the cavity (which has a diameter of around 7 Å) is occupied by a chloride ion. Other articles describing the copper-20 wheel structure include Jabbour, D.; Keita, B.; Nadjo, L.; Kortz, U.; Mal, S. S. Electrochem. Comm. 2005, 7, 841-847; Alam, M. S.; Dremov, V.; Müller, P.; Postnikov, A. V.; Mal, S. S.; Hussain, F.; Kortz, U. Inorg. Chem. 2006, 45, 2866-2872 and Liu, G.; Liu, T.; Mal, S. S.; Kortz, U. J. Am. Chem. Soc. 2006, 128, 10103-10110, all incorporated herein by reference.

Examples of suitable POMs for use in the present process include:

$K_{12}Li_{13}[Cu_{20}Cl(OH)_{24}(H_2O)_{12}(P_8W_{48}O_{148})].22H_2O$ abbreviated as ($Cu_{20}P_8W_{48}$ or $Cu_{20}Cl$ or $Cu_{20}ClP_8W_{48}$);

$Na_{11}Cs_2[Cu_4(H_2O)_2(GeW_9O_{34})_2]Cl.31H_2O$ abbreviated as ($Cu_4(GeW_9)_2$);

$Na_{12}[Cu_3(H_2O)_3As_2W_{18}O_{66}].32H_2O$ abbreviated as ($Cu_3(AsW_9)_2$);

$K_{10}[Cu_5(OH)_4(H_2O)_2(A-\alpha-SiW_9O_{33})_2].18.5H_2O$ abbreviated as ($Si_2W_{18}Cu_5$). In this formula, "A" is the conventional designation for the isomeric form of the material;

$Na_{12}[Cu_3(H_2O)_3Sb_2W_{18}O_{66}].46H_2O$ abbreviated as ($Cu_3(SbW_9)_2$);

$\{[K_7Na[Cu_4K_2(H_2O)_6(\alpha-AsW_9O_{33})_2].5.5H_2O\}_n$ abbreviated as ($K_7Na[Cu_4(AsW_9O_{33})_2]$);

$K_6Na_2[Cu_4K_2(H_2O)_{5.4}Cl_{0.6}(\alpha-SbW_9O_{33})_2].17H_2O$ abbreviated as (K—$Cu_4Sb_2W_{18}$);

$Na(NH_4)_{8.5}[Cu_{4.5}(H_2O)_4Cl_{0.5}(ASW_9O_{33})_2].11H_2O$ abbreviated as ($NH_4$—$Cu_5As_2W_{18}$);

Na(NH$_4$)$_{8.5}$[Cu$_{4.5}$(H$_2$O)$_4$Cl$_{0.5}$(SbW$_9$O$_{33}$)$_2$].11H$_2$O abbreviated as (NH$_4$—Cu$_5$Sb$_2$W$_{18}$);

K$_{12}$Li$_{13}$[Cu$_{20}$Br(OH)$_{24}$(H$_2$O)$_{12}$(P$_8$W$_{48}$O$_{184}$)].22H$_2$O abbreviated as (Cu$_{20}$Br);

K$_4$Na$_4$[Ru$_2$(H$_2$O)$_6$Sb$_2$W$_{20}$O$_{70}$].12H$_2$O abbreviated as (Ru$_2$(H$_2$O));

K$_4$[{Ru(C$_6$H$_6$)(H$_2$O)}{Ru(C$_6$H$_6$)}(γ-GeW$_{10}$O$_{36}$)].7H$_2$O abbreviated as (K$_4$C$_{12}$Ru$_2$H$_{28}$GeW$_{10}$O$_{44}$);

K$_4$[{Ru(C$_6$H$_6$)(H$_2$O)}{Ru(C$_6$H$_6$)}(γ-SiW$_{10}$O$_{36}$)].9H$_2$O abbreviated as (K$_4$C$_{12}$Ru$_2$H$_{32}$SiW$_{10}$O$_{46}$); and {CsK$_4$[β-GeW$_{11}$MnO$_{38}$(OH)].13H$_2$O}$_\infty$ abbreviated as (CsK$_4$H$_{27}$GeW$_{11}$MnO$_{52}$).

The transition metal substituted polyoxotungstate POMs required for the process of the invention, such as those POMs identified above, can be used as catalysts in the present oxidation process in unsupported form or on a support. Suitable supports include acidic materials, such as alumina, basic materials, such as magnesia, and neutral materials, such as silica. By virtue of the ionic nature of the POM, if the support is acidic, anchoring the catalyst to the support can readily be achieved by simply dissolving the POM in water and stirring the solution with the support material at a temperature of, for example 20° C. to 100° C. After filtration and drying, a supported catalyst containing up to for example 10 wt % of the POM can readily be obtained. If, on the other hand, the support material is basic, it may be necessary to initially functionalize the support, for example by providing surface amine groups on the support and then acidifying the support to protonate the amine groups, before combining the support with the POM solution. In this way, POM loadings of up to for example 20 wt % can readily be obtained.

In one embodiment, the support material is porous and particularly mesoporous. Suitable mesoporous materials include MCM-41, which is described in U.S. Pat. No. 5,098,684; MCM-48, which is described in U.S. Pat. No. 5,198,203 and MCM-50, which is described in U.S. Pat. No. 5,304,363, and SBA-15 which is described in Zhao, D., et al., J. Am. Chem. Soc., 120 6024 (1998).

In addition to the POM catalyst, it may be desirable to add to the reaction mixture a free radical initiator, which is typically a peroxide, such as tert-butyl peroxide, or a hydroperoxide, such as tert-butyl hydroperoxide.

Suitable conditions for the present oxidation step include a temperature between about 50° C. and about 200° C., such as about 90° C. to about 125° C., and/or a pressure of about 15 to about 1000 kPa, such as about 40 to about 250 kPa. The oxidation reaction is conveniently conducted in a catalytic distillation unit and the hydroperoxide produced may be concentrated by distilling off the unreacted alkylaromatic compound.

The product of the oxidation reaction includes a hydroperoxide of general formula (II):

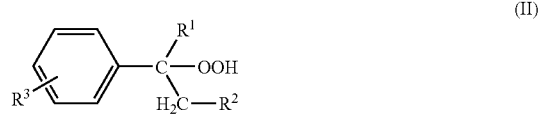

(II)

in which R$^1$, R$^2$ and R$^3$ have the same meaning as in formula (I). Preferably, the hydroperoxide is sec-butylbenzene hydroperoxide, cumene hydroperoxide or cyclohexylbenzene hydroperoxide. This hydroperoxide can then be converted by acid cleavage to phenol (which may be a substituted phenol) and an aldehyde or ketone of the general formula R$^1$COCH$_2$R$^2$ (III), in which R$^1$ and R$^2$ have the same meaning as in formula (I).

The cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 hr$^{-1}$, preferably about 1 to about 50 hr$^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

In the case where the alkylaromatic compound that is oxidized according to the invention is cyclohexylbenzene, the oxidation product is cyclohexylbenzene hydroperoxide and the cleavage product comprises phenol and cyclohexanone. The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The invention will now be more particularly described with reference to the following non-limiting Examples.

EXAMPLE 1

Preparation of K$_{12}$Li$_{13}$[Cu$_{20}$Cl(Oh)$_{24}$(H$_2$O)$_{12}$(P$_8$W$_{48}$O$_{184}$)].22H$_2$O (Abbreviated as Cu$_{20}$P$_8$W$_{48}$ or Cu$_{20}$Cl or Cu$_{20}$ClP$_8$W$_{48}$)

A sample of CuCl$_2$.2H$_2$O (0.10 g, 0.60 mmol) was dissolved in a 1M LiCH$_3$COO buffer solution (20 mL) at pH 6.0, then K$_{28}$Li$_5$[H$_7$P$_8$W$_{48}$O$_{184}$].92H$_2$O (0.37 g 0.025 mmol) was added. This solution was heated to 80° C. for 1 hour and after cooling to room temperature it was filtered. The filtrate was allowed to evaporate in an open beaker at room temperature. After 1-2 days a blue crystalline product started to appear. Evaporation was allowed to continue until the solution level had approached the solid product, which was then collected by filtration and air-dried. Yield: 0.11 g (30%). IR: 1137(sh), 1121(s), 1080(s), 1017(m), 979(sh), 951(sh), 932(s), 913(sh), 832(sh), 753(s), 681(s), 570(sh), 523(w), 470(w) cm$^{-1}$. (Reference: Mal, S. S.; Kortz, U. *Angew. Chem. Int. Ed.* 2005, 44, 3777-3780.)

EXAMPLE 2

Preparation of $Na_{11}Cs_2[Cu_4(H_2O)_2(GeW_9O_{34})_2]$ $Cl.31H_2O$ (Abbreviated as $Cu_4(GeW_9)_2$)

The following reagents were dissolved in 40 mL of a 0.5 M sodium acetate buffer (pH 4.8) with stirring in this order: 0.334 g (1.96 mmol) of $CuCl_2\ 2H_2O$, 0.0928 g (0.888 mmol) of $GeO_2$, and 2.64 g (8.00 mmol) of $Na_2WO_4\ 2H_2O$. This solution was heated to 90° C. for 1 hour and then cooled to room temperature. Single crystals suitable for X-ray crystallography were obtained by layering of the above solution with a dilute CsCl solution and slow evaporation (yield: 1.8 g, 71%). IR: 941 (s), 890 (s), 846 (w), 775 (vs), 734 (s), 718 (s), 509 (w), 469 (w), 438 (w) $cm^{-1}$. (Reference: Kortz, U.; Nellutla, S.; Stowe, A. C.; Dalal, N. S.; Rauwald, U.; Danquah, W.; Ravot, D. Inorg. Chem. 2004, 43, 2308-2317.)

EXAMPLE 3

Preparation of $Na_{12}[Cu_3(H_2O)_3As_2W_{18}O_{66}].32H_2O$ (Abbreviated as $Cu_3(AsW_9)_2$)

A 1.2 g (6.8 mmol) sample of $CuCl_2\ 2H_2O$ was dissolved in 50 mL of $H_2O$, and then, 10.0 g (4.1 mmol) of $Na_9[\alpha\text{-}AsW_9O_{33}]\ 19.5H_2O$ was added. The solution was refluxed for 1 hour and filtered after it cooled (pH 6.2). Slow evaporation at room temperature led to large green crystals suitable for X-ray diffraction. The potassium salt of the polyanion can also be isolated in high yield by precipitation of the above solution with solid KCl (15 g). This resulted in 10.1 g of greenish product, which was isolated and air-dried (yield 89%). IR: 956, 904, 873, 785, 750, 735, 503, 472, 405 $cm^{-1}$. (Reference: Kortz, U.; Al-Kassem, N. K.; Savelieff, M. G.; Al Kadi, N. A.; Sadakane, M. Inorg. Chem. 2001, 40, 4742-4749.)

EXAMPLE 4

Preparation of $K_{10}[Cu_5(OH)_4(H_2O)_2(A\text{-}\alpha\text{-}SiW_9O_{33})_2].18.5H_2O$ (Abbreviated as $Si_2W_{18}Cu_5$)

A 0.50 g (0.16 mmol) sample of $K_{10}[A\text{-}\alpha\text{-}SiW_9O_{34}]$ was added with stirring to a solution of 0.076 g (0.44 mmol) of $CuCl_2\ 2H_2O$ in 20 mL of a 0.5 M NaAc buffer (pH 4.8). This solution was heated to 80° C. for 30 min and then cooled to room temperature and filtered. Slow evaporation at room temperature resulted after about 1-2 weeks in green crystals that were filtered off and air-dried. Yield: 0.28 g (63%). IR: 1008, 945, 915, 885, 810, 768, 698, 595, 546, 524 $cm^{-1}$. (Reference: Bi, L.-H.; Kortz, U. Inorg. Chem. 2004, 43, 7961-7962.)

EXAMPLE 5

Preparation of $Na_{12}[Cu_3(H_2O)_3Sb_2W_{18}O_{66}].46H_2O$ (Abbreviated as $Cu_3(SbW_9)_2$)

A 1.0 g (5.8 mmol) sample of $CuCl_2.2H_2O$ was dissolved in 50 mL of $H_2O$, and then, 10.0 g (3.5 mmol) of $Na_9[\alpha\text{-}SbW_9O_{33}].19.5H_2O$ was added. The solution was refluxed for 1 hour and filtered after it cooled (pH 6.2). Slow evaporation at room temperature led to large green crystals. The potassium salt of the polyanion can also be isolated in high yield by precipitation of the above solution with solid KCl (15 g). This resulted in 9.8 g of greenish product, which was isolated and air-dried (yield 97%). IR: 965, 944, 891, 858, 772, 732, 504, 475, 438 $cm^{-1}$. (Reference: Kortz, U.; Al-Kassem, N. K.; Savelieff, M. G.; Al Kadi, N. A.; Sadakane, M. Inorg. Chem. 2001, 40, 4742-4749.)

EXAMPLE 6

Preparation of $\{[K_7Na[Cu_4K_2(H_2O)_6(\alpha\text{-}AsW_9O_{33})_2][.5.5H_2O]\}_n$ (Abbreviated as $K_7Na[Cu_4(AsW_9O_{33})_2]$)

A 0.51 g (3.0 mmol) sample of $CuCl_2\ 2H_2O$ was dissolved in 40 mL of $H_2O$, and then 4.0 g (1.5 mmol) of $K_9[\alpha\text{-}AsW_9O_{33}]$ was added. The solution was refluxed for 1 hour and filtered after cooling. Slow evaporation at room temperature resulted in 2.9 g of a green, crystalline product which was isolated and air-dried (yield 73%). IR: 974(sh), 950(s), 907(s), 888(sh), 864(sh), 788(sh), 749(s), 736 (s), 484(w), 465(w) $cm^{-1}$. (Reference: Kortz, U.; Nellutla, S.; Stowe, A. C.; Dalal, N. S.; van Tol, J.; Bassil, B. S. Inorg. Chem. 2004, 43, 144-154.)

EXAMPLE 7

Preparation of $K_6Na_2[Cu_4K_2(H_2O)_{5.4}Cl_{0.6}(\alpha\text{-}SbW_9O_{33})_2].7H_2O$ (Abbreviated as $K\text{-}Cu_4Sb_2W_{18}$)

A 0.51 g (3.0 mmol) sample of $CuCl_2.2H_2O$ was dissolved in 40 mL of $H_2O$ and then 4.1 g (1.5 mmol) of $K_9[\alpha\text{-}SbW_9O_{33}]$ was added. The solution was refluxed for 1 hour and filtered after cooling. Slow evaporation at room temperature resulted in 2.9 g of a green, crystalline product which was isolated and air-dried (yield 70%). IR: 944, 897, 851, 775(sh), 730, 615, 563, 495(sh), 445 $cm^{-1}$.

EXAMPLE 8

Preparation of $Na(NH_4)_{8.5}[Cu_{4.5}(H_2O)_4Cl_{0.5}(AsW_9O_{33})_2].11H_2O$ (Abbreviated as $NH_4\text{—}Cu_5As_2W_{18}$)

A 0.31 g (0.13 mmol) sample of $(NH_4)_9[AsW_9O_{33}]$ was added with stirring to a solution of 0.22 g (1.30 mmol) $CuCl_2.H_2O$ in 20 mL of a 0.5 M $NH_4OAc$ buffer (pH 4.8). This solution was heated to 80° C. for 1 hour and then cooled to room temperature and filtered. Slow evaporation in an open vial resulted in 0.23 g (yield 68%) of green crystalline material suitable for X-ray diffraction. IR: 1400, 968(sh), 948, 904, 862(sh), 789(sh), 749(sh), 736, 629, 568, 484, 453 $cm^{-1}$.

EXAMPLE 9

Preparation of $Na(NH_4)_{8.5}[Cu_{4.5}(H_2O)_4Cl_{0.5}(SbW_9O_{33})_2].11H_2O$ (Abbreviated as $NH_4\text{—}Cu_5Sb_2W_{18}$)

A 0.32 g (0.13 mmol) sample of $(NH_4)_9[SbW_9O_{33}]$ was added with stirring to a solution of 0.22 g (1.30 mmol) $CuCl_2.H_2O$ in 20 mL of a 0.5 M $NH_4OAc$ buffer (pH 4.8). This solution was heated to 80° C. for 1 hour and then cooled to room temperature and filtered. Slow evaporation in an open vial resulted in 0.24 g (yield 69%) of green crystalline material suitable for X-ray diffraction. IR: 1402, 944, 897, 848, 773(sh), 731, 638, 568, 476, 447 $cm^{-1}$.

EXAMPLE 10

Preparation of $_{12}Li_{13}[Cu_{20}Br(OH)_{24}(H_2O)_{12}(P_8W_{48}O_{184})].22H_2O$ (Abbreviated as $Cu_{20}Br$)

A sample of $CuBr_2.2H_2O$ (0.145 g, 0.60 mmol) was dissolved in a 1M $LiCH_3COO$ buffer solution (20 mL) at pH 6.0, then $K_{28}Li_5[H_7P_8W_{48}O_{184}]$ 92H$_2$O (0.37 g, 0.025 mmol) was added. This solution was heated up at 80° C. for 1 hour and filtered hot. The filtrate was allowed to evaporate in an open beaker at room temperature. After one day a blue crystalline product started to appear. Evaporation was allowed to continue until the solution level had approached the solid product, which was then collected by filtration and air-dried. IR: 1120, 1079, 1017, 950, 935, 902, 835, 752, 680, 525, 471 cm$^{-1}$.

EXAMPLE 11

Preparation of IC$_4$Na$_4$[Ru$_2$(H$_2$O)$_6$Sb$_2$W$_{20}$O$_{70}$]. 12H$_2$O (Abbreviated as Ru$_2$(H$_2$O))

0.05 g (0.08 mmol) of [(p-cymene)RuCl$_2$]$_2$ was dissolved with stirring in 20 mL of 0.5 M NaAc buffer (pH 6.0). Then 0.5 g (0.08 mmol) of Na$_{12}$[Sb$_2$W$_{22}$O$_{74}$(OH)$_2$] was added. The solution was heated to 90° C. for 30 min and filtered after it had cooled. Then 0.5 mL of 1.0 M KCl solution was added to the filtrate. Slow evaporation at room temperature led to 0.12 g (yield 26%) of a yellow crystalline product after one week. IR: 950, 885(sh), 863(sh), 836(sh), 806, 769, 703, 655, 453, 413 (cm$^{-1}$).

EXAMPLE 12

Preparation of K$_4$[{Ru(C$_6$H$_6$)(H$_2$O)}{Ru(C$_6$H$_6$)}(γ-GeW$_{10}$O$_{36}$)].7H$_2$O (Abbreviated as K$_4$C$_{12}$Ru$_2$H$_{28}$GeW$_{10}$O$_{44}$)

A 0.27 g (0.54 mmol) sample of [RuC$_6$H$_6$Cl$_2$]$_2$ was dissolved in 20 mL of water, followed by addition of 1.56 g (0.54 mmol) of K$_8$[γ-GeW$_{10}$O$_{36}$].6H$_2$O. The pH value was adjusted to pH 2.5 by addition of 1M HCl. This solution was heated to 80° C. for 1 hour and then cooled to room temperature. The solution was filtered and then 1.0 mL of 1.0 M CsCl was added. A small amount of orange precipitate (believed to be a benzene-Ru(II)-containing germanotungstate) appeared and was immediately filtered off. Then, 2.0 mL of 1.0 M KCl was added to the filtrate, which was allowed to evaporate in an open beaker at room temperature. Brown needle-shaped crystals started to appear after 1 day. Evaporation was continued until the solvent approached the solid product (yield 0.82 g, 48%). IR: 3072(w), 2924(w), 2848(w), 2361(w), 2333(w), 1435(w), 948(s), 872(sh), 844(s), 795(s), 725(s), 674 (m), 611(w), 531(m), 463(m) cm$^{-1}$. (Reference: Bi, L.-H.; Chubarova, E. V.; Nsouli, N. H.; Dickman, M. H.; Kortz, U.; Keita, B.; Nadjo, L. Inorg. Chem. 2006, 45, 8575-8583.)

EXAMPLE 13

Preparation of K$_4$[{Ru(C$_6$H$_6$H$_2$O)}{Ru(C$_6$H$_6$)}(γ-SiW$_{10}$O$_{36}$)]9H$_2$O (Abbreviated as K$_4$C$_{12}$Ru$_2$H$_{32}$SiW$_{10}$O$_{46}$)

A 0.18 g (0.36 mmol) sample of [RuC$_6$H$_6$Cl$_2$]$_2$ was dissolved in 20 mL of water followed by addition of 1.0 g (0.36 mmol) of K$_8$[γ-SiW$_{10}$O$_{36}$].12H$_2$O. The pH value was adjusted to pH 2.5 by addition of 1M HCl. This solution was heated to 80° C. for 1 hour, and then cooled to room temperature. The solution was filtered and then 2.0 mL of 1.0 M KCl was added. This solution was allowed to evaporate in an open beaker at room temperature. A yellow crystalline product started to appear after a week. Evaporation was continued until the solvent approached the solid product (yield 0.18 g, 32%). IR: 1435(m), 1152(w), 992(m), 948(s), 904(sh), 881 (sh), 868(s), 776(s), 752(s), 685(m), 614(w), 558(m), 498(w), 473(w) cm$^{-1}$. (Reference: Bi, L.-H.; Chubarova, E. V.; Nsouli, N. H.; Dickman, M. H.; Kortz, U.; Keita, B.; Nadjo, L. Inorg. Chem. 2006, 45, 8575-8583.).

EXAMPLE 14

Preparation of {CsK$_4$[β-GeW$_{11}$MnO$_{38}$(OH)]. 13H$_2$O}$_∞$ (Abbreviated as CsK$_4$H$_{27}$GeW$_{11}$MnO$_{52}$)

A 0.5 g (0.17 mmol) sample of K$_8$[γ-GeW$_{10}$O$_{36}$].6H$_2$O was added with stirring to a solution of 0.074 g (0.34 mmol) of MnCl$_2$.2H$_2$O in 20 mL of 1M KOAc (pH 4.8). This solution was stirred at 50° C. for 30 min. Layering of the above solution with 1M CsCl resulted in crystals.

EXAMPLES 15-27

Oxidation of Sec-Butylbenzene Over Non-supported Polyoxometalates

To a 250-ml round bottom flask fitted with a condenser, stirrer and an air sparger, was charged 100 g (unless indicated differently in Table 1) of a substantially pure sec-butylbenzene (SBB) supplied by TCI America, 1 g tert-butyl peroxide (98%) supplied by Aldrich and one of the POM catalysts produced in Examples 2 to 14. The flask was heated using a temperature-controlled heating mantle. The reaction temperature was 115° C. and the pressure was atmospheric. The air flow rate was approximately 220 cc/min. After 6 hrs, a small aliquot of the reaction mixture was removed from the flask and analyzed by gas chromatography (GC). The process was repeated for each of the catalysts produced in Examples 2 to 14. The catalyst type and amount, and the SBB conversion and the selectivity to sec-butylbenzene hydroperoxide (SBBHP) are shown in Table 1. Also indicated in the Table 1 are the selectivity of each catalyst to the by-products acetophenone (AP) and 2-phenyl-2-butylhydroxide (PBOH).

TABLE 1

| Ex | Catalyst | Cat Ex. | Cat. Amt. (g) | SBB Amt. (g) | SBB Con % | SBBHP Sel % | PBOH Sel % | AP Sel % |
|---|---|---|---|---|---|---|---|---|
| 15 | Cu$_4$(GeW$_9$)$_2$ | 2 | 0.019 | 100 | 4.9 | 80.1 | 2.2 | 16.9 |
| 16 | Cu$_3$(AsW$_9$)$_2$ | 3 | 0.15 | 100 | 4.4 | 84.0 | 1.9 | 13.4 |
| 17 | Si$_2$W$_{18}$Cu$_5$ | 4 | 0.081 | 100 | 5.9 | 82.1 | 1.9 | 15.1 |
| 18 | Cu$_3$(SbW$_9$)$_2$ | 5 | 0.174 | 100 | 5.2 | 83.8 | 1.8 | 13.6 |
| 19 | K$_7$Na[Cu$_4$(AsW$_9$O$_{33}$)$_2$] | 6 | 0.1225 | 100 | 4.6 | 84.7 | 1.8 | 12.8 |
| 20 | K—Cu$_4$Sb$_2$W$_{18}$ | 7 | 0.0515 | 100 | 5.3 | 83.8 | 1.8 | 13.7 |
| 21 | NH$_4$—Cu$_5$As$_2$W$_{18}$ | 8 | 0.145 | 100 | 4.9 | 83.0 | 2.0 | 14.2 |
| 22 | NH$_4$—Cu$_5$Sb$_2$W$_{18}$ | 9 | 0.0925 | 100 | 8.2 | 78.0 | 2.6 | 18.5 |
| 23 | Cu$_{20}$Br | 10 | 0.14 | 100 | 5.1 | 80.3 | 2.2 | 16.6 |
| 24 | Ru$_2$(H$_2$O) | 11 | 0.192 | 100 | 7.2 | 75.4 | 3.1 | 20.5 |
| 25 | K$_4$C$_{12}$Ru$_2$H$_{28}$GeW$_{10}$O$_{44}$ | 12 | 0.09 | 50 | 17.0 | 67.5 | 3.9 | 27.3 |

TABLE 1-continued

| Ex | Catalyst | Cat Ex. | Cat. Amt. (g) | SBB Amt. (g) | SBB Con % | SBBHP Sel % | PBOH Sel % | AP Sel % |
|---|---|---|---|---|---|---|---|---|
| 26 | $K_4C_{12}Ru_2H_{32}SiW_{10}O_{46}$ | 13 | 0.1 | 50 | 10 | 79 | 2.4 | 17.7 |
| 27 | $CsK_4H_{27}GeW_{11}MnO_{52}$ | 14 | 0.092 | 50 | 12.7 | 86.6 | 0.3 | 12.8 |

EXAMPLE 28

Synthesis of Mesoporous Silica and Immobilization of Polyoxometalates

A solution was prepared by stirring a mixture of 1.0 g of the tri-block copolymer, poly(ethylene oxide)-poly(propylene oxide)-poly(ethylene oxide) ($EO_{20}PO_{70}EO_{20}$) (BASF), 30 ml of 2M hydrochloric acid, and 7.5 ml of water at 40° C. for 4 hours. 2.08 g of tetraethylorthosilicate (TEOS) was then added to the solution to produce a synthesis mixture having the following molar composition:

2($EO_{20}PO_{70}EO_{20}$): 60HCl: 4.25TEOS: 15$H_2O$

After stirring for 24 hours at 40° C., the synthesis mixture was transferred to an autoclave and then heated at 95° C. for 3 days. The solid products were then filtered from the synthesis mixture and calcined at 550° C. for 4 hours. The product was the mesoporous silica material SBA-15 having a BET surface area of 893 $m^2$/g, a pore volume of 1.37 cc/g and a pore size of 6.6 nm.

The SBA-15 material was then used as a support for anchoring one or more POMs, such as those prepared in Examples 1 to 14. This was achieved by initially refluxing the silica material under a nitrogen blanket with aminopropyltriethoxysilicate in toluene for 5 hours, whereby the silanol groups on the SBA-15 reacted with the ethoxy groups on the aminopropyltriethoxysilicate to produce Si—O—Si bonds. The resultant aminated SBA-15 was then stirred in 200 ml (2M) hydrochloric acid for 12 hours to convert the amine to an ammonium salt and the product was then stirred with the desired POM. Filtration, washing and drying at 95° C. for 5 hours recovered the POM catalyst supported on mesoporous silica. The overall anchoring process is indicated below:

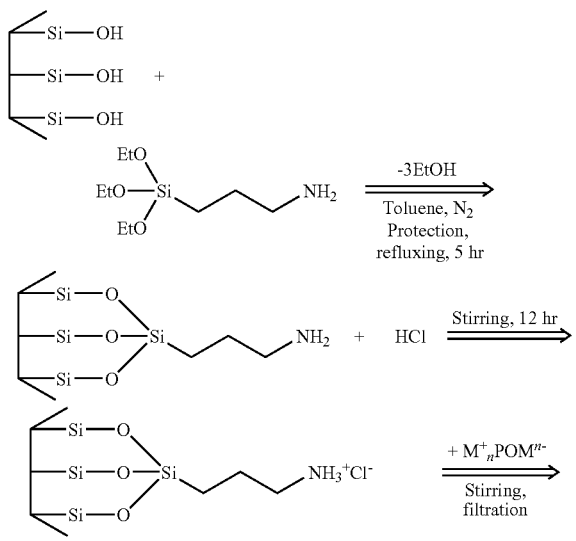

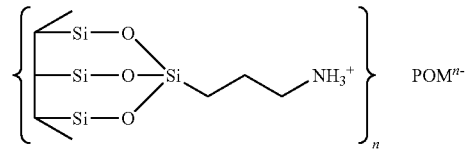

EXAMPLE 29

Oxidation of Sec-Butylbenzene in the Presence of NHPI

To a 250-ml round bottom flask fitted with a condenser, stirrer and an air sparger, was charged 100 g of a substantially pure sec-butylbenzene supplied by TCI America and 0.375 g N-hydroxyphthalimide (NHPI, available from Aldrich). The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The data are shown in FIG. 1, in which the catalyst is indicated as NHPI.

EXAMPLE 30

Oxidation of Sec-Butylbenzene in the Presence of $Cu_{20}P_8W_{48}$/SBA-15

To a 250-ml round bottom flask fitted with a condenser, stirrer and an air sparger, was charged 100 g of a substantially pure sec-butylbenzene supplied by TCI America, 1 g tert-butyl peroxide (98%) supplied by Aldrich and 0.2 g of the catalyst produced by supporting $Cu_{20}P_8W_{48}$ of Example 1 with the mesoporous silica material SBA-15 in accordance with Example 28. The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The data are shown in FIG. 1, in which the catalyst is indicated as Cu/SBA.

EXAMPLE 31

Oxidation of Sec-Butylbenzene over $Cu_{20}P_8W_{48}$/SBA Fresh vs Recycled Catalyst The catalyst from Example 30 was filtered from the product mixture and retested at the same conditions as Example 30. The data are shown in FIG. 2. The data show that a minor activity loss is observed with the recycled catalyst; however the selectivity to the hydroperoxide has improved dramatically.

EXAMPLE 32

Oxidation of Sec-Butylbenzene Over $Cu_{20}P_8W_{48}$ Supported on $Al_2O_3$ To a 250-ml round bottom flask fitted with a condenser, stirrer and an air sparger, was charged 100 g of a substantially pure sec-butylbenzene supplied by TCI America, 1 g tert-butyl peroxide (98%) supplied by Aldrich and 0.2 g of a catalyst comprising $Cu_{20}P_8W_{48}$ of Example 1 supported on $Al_2O_3$. The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The data are shown in FIG. 3. The data show that lower activity (SBB conversion) and selectivity (to SBBHP) were obtained when the catalyst was supported on $Al_2O_3$ as compared with SBA-15.

EXAMPLE 33

Oxidation of Sec-Butylbenzene Over Non-supported $Cu_{20}P_8W_{48}$

To a 250-ml round bottom flask fitted with a condenser, stirrer and an air sparger, was charged 100 g of a substantially pure sec-butylbenzene supplied by TCI America, 1 g tert-butyl peroxide (98%) supplied by Aldrich and 0.17 g unsupported $Cu_{20}P_8W_{48}$ of Example 1. The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The data are shown in FIG. 4 and show that a slight improvement in the selectivity and an increase in the activity were observed with the unsupported, versus the supported catalyst.

EXAMPLE 34

Oxidation of Sec-Butylbenzene/Cumene Mixture in the Presence of NHPI

To a 250-ml round bottom flask fitted with a condenser, stirrer and an air sparger, was charged 100 g of a substantially pure sec-butylbenzene and 22.4 g cumene, both supplied by TCI America, and 0.05 g N-hydroxyphthalimide (NHPI, available from Aldrich). The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The data are shown in FIGS. 5 and 6.

EXAMPLE 35

Oxidation Of Sec-Butylbenzene/Cumene Mixture Over Non-supported $Cu_{20}P_8W_{48}$ To a 250-ml round bottom flask fitted with a condenser, stirrer and an air sparger, was charged 100 g of a substantially pure sec-butylbenzene and 22.4 g cumene, both supplied by TCI America, and 0.2 g $Cu_{20}P_8W_{48}$ from Example 1. The flask was heated using a temperature-controlled heating mantle. The reaction temperature was 115° C. and the pressure was atmospheric. The air flow rate was approximately 220 cc/min. Every 45 minutes, a small aliquot of the reaction mixture was removed from the flask and analyzed by GC. The data are also shown in FIGS. 5 and 6. The data show that the $Cu_{20}P_8W_{48}$ catalyst shows similar SBB and cumene conversion levels to the NHPI catalyst (FIG. 5) and (FIG. 6) similar final selectivity to SBBHP and cumene hydroperoxide (CHP).

EXAMPLE 36

Oxidation of Cyclohexylbenzene Over Non-supported Polyoxometalate

The oxidation process described for Examples 15-27 was performed on substantially pure cyclohexylbenzene (CHB) instead of sec-butylbenzene; and using as the polyoxometalate (POM) catalyst the $Cu_{20}P_8W_{48}$ produced by the process of Example 1. The oxidation reaction temperature was 115° C. (as in Example 15). The process was then repeated, but employing a reaction temperature of 110° C. In both cases, every 45 minutes, a small aliquot of the reaction mixture was removed from the flask and analyzed by GC. The data for CHB conversion (in wt %) and cyclohexylbenzene hydroperoxide (CHBHP) selectivity (in wt %) at the two temperatures are shown in FIG. 7. The data show that in these runs, the selectivity dropped off more at the higher temperature.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for oxidizing an alkylaromatic compound to the corresponding hydroperoxide, the process comprising contacting an alkylaromatic compound of general formula (I):

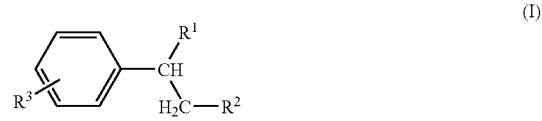

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a polyoxometalate, wherein the polyoxometalate comprises a polyoxotungstate substituted with at least one further transition metal.

2. The process of claim 1, wherein said at least one further transition metal is selected from copper, manganese, iron, cobalt, nickel, zinc, cadmium, ruthenium and mercury.

3. The process of claim 1, wherein said polyoxotungstate also contains at least one element from Groups 13 to 15 of the Periodic Table of Elements.

4. The process of claim 3, wherein said at least one element from Groups 13 to 15 of the Periodic Table of Elements is selected from antimony, arsenic, bismuth, silicon, boron and phosphorus.

5. The process of claim 1, wherein said catalyst further comprises a support.

6. The process of claim 1, wherein said catalyst further comprises a porous support.

7. The process of claim 5, wherein said support comprises mesopores.

8. The process of claim 1, wherein said alkylaromatic compound of general formula (I) is selected from ethylbenzene, cumene, sec-butylbenzene, sec-pentylbenzene, p-methyl-sec-butylbenzene, 1,4-diphenylcyclohexane, sec-hexylbenzene, cyclopentylbenzene, cyclohexylbenzene and cyclooctylbenzene.

9. The process of claim 1, wherein said alkylaromatic compound of general formula (I) is sec-butylbenzene or cyclohexylbenzene.

10. The process of claim 1, wherein said contacting is conducted at a temperature of about 50° C. to about 200° C.

11. The process of claim 1, wherein said contacting is conducted at a temperature of about 90° C. to about 125° C.

12. The process of claim 1, wherein said contacting is conducted at a pressure of about 15 kPa to about 500 kPa.

13. The process of claim 1, wherein said contacting is conducted at a pressure of about 100 kPa to about 200 kPa.

14. A process for producing a phenol, said process comprising:

(a) contacting an alkylaromatic compound of general formula (I):

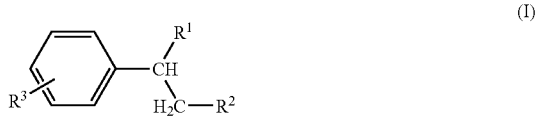
(I)

in which $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of a catalyst comprising a polyoxometalate to produce a hydroperoxide of general formula (II):

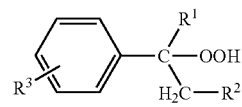
(II)

in which $R^1$, $R^2$ and $R^3$ have the same meaning as in formula (I) and wherein the polyoxometalate comprises a polyoxotungstate substituted with at least one further transition metal, and (b) converting the hydroperoxide of formula (II) into a phenol and an aldehyde or ketone of the general formula $R^1COCH_2R^2$ (III), in which $R^1$ and $R^2$ have the same meaning as in formula (I).

15. The process of claim 14, wherein said at least one further transition metal is selected from copper, manganese, iron, cobalt, nickel, zinc, cadmium, ruthenium and mercury.

16. The process of claim 14, wherein said polyoxotungstate also contains at least one element from Groups 13 to 15 of the Periodic Table of Elements.

17. The process of claim 16, wherein said at least one element from Groups 13 to 15 of the Periodic Table of Elements is selected from antimony, arsenic, bismuth, silicon, boron and phosphorus.

18. The process of claim 14, wherein said catalyst further comprises a support.

19. The process of claim 14, wherein said catalyst further comprises a porous support.

20. The process of claim 18, wherein said support comprises mesopores.

21. The process of claim 14, wherein said contacting is conducted at a temperature of about 50° C. to about 200° C.

22. The process of claim 14, wherein said contacting is conducted at a pressure of about 15 kPa to about 500 kPa.

23. The process of claim 14, wherein said alkylaromatic compound of general formula (I) is selected from ethylbenzene, cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene.

24. The process of claim 14, wherein said alkylaromatic compound of general formula (I) is sec-butylbenzene or cyclohexylbenzene.

25. The process of claim 24, wherein the compound of formula (II) is tert-butyl hydroperoxide or cumene hydroperoxide.

* * * * *